United States Patent [19]
Contestable et al.

[11] Patent Number: 5,916,757
[45] Date of Patent: Jun. 29, 1999

[54] SPECIFIC BINDING ASSAY USING ENZYME INHIBITOR AND ANTI-INHIBITOR ANTIBODIES

[75] Inventors: Paul B. Contestable; John L. Daiss, both of Rochester; Holly L. Groth, Hamlin; Elizabeth A. Grogan; Brian A. Snyder, both of Rochester, all of N.Y.

[73] Assignee: Johnson & Johnson Clinical Diagnostics, Inc., Rochester, N.Y.

[21] Appl. No.: 08/683,247

[22] Filed: Jul. 17, 1996

Related U.S. Application Data

[63] Continuation of application No. 08/250,980, May 31, 1994, abandoned.

[51] Int. Cl.$^6$ .................................................. G01N 33/53
[52] U.S. Cl. ..................... 435/7.71; 435/7.92; 435/12; 435/17; 435/21; 435/25; 435/26; 435/28; 436/518; 436/523; 436/524; 436/528; 436/533; 436/534
[58] Field of Search .................... 435/4, 7.1, 7.7, 435/7.71, 7.72, 7.8, 7.92, 975, 12, 21, 26, 28, 17, 25; 436/518, 523, 524, 528, 533, 534

[56] References Cited

U.S. PATENT DOCUMENTS

| | | | |
|---|---|---|---|
| 3,935,074 | 1/1976 | Rubenstein et al. | 195/103.5 |
| 4,161,515 | 7/1979 | Ullman | 424/8 |
| 4,218,436 | 8/1980 | Fitzpatrick | 424/85 |
| 4,233,401 | 11/1980 | Yoshida et al. | 435/7 |
| 4,621,048 | 11/1986 | Ashihara et al. | 435/5 |
| 4,649,105 | 3/1987 | Kasahara et al. | 435/7.71 |
| 4,686,181 | 8/1987 | Doná | 435/7 |
| 5,236,826 | 8/1993 | Marshall | 435/7.92 |
| 5,565,326 | 10/1996 | Daiss et al. | |
| 5,650,324 | 7/1997 | Gorman et al. | |

FOREIGN PATENT DOCUMENTS

| | | | |
|---|---|---|---|
| 166583 | 1/1986 | European Pat. Off. | G01N 33/88 |
| 336647 | 10/1989 | European Pat. Off. | G01N 33/88 |
| 353614 | 2/1990 | European Pat. Off. | G01N 33/542 |
| 487301 | 11/1991 | European Pat. Off. | G01N 33/535 |
| 0487301 | 2/1992 | European Pat. Off. | |
| 532187 | 3/1993 | European Pat. Off. | G01N 33/58 |
| T053-230 | 9/1990 | Hungary | |
| 90/07714 | 12/1988 | WIPO | G01N 33/542 |

OTHER PUBLICATIONS

Friquet et al in Creighton, TE ed. "Protein Structure", IRL Press NY 1989 pp. 287–310.
Amersham corp, Amersham Life Science Catalogue 1994, pp. 226–231.
Henderson et al, *Clin.Chem.*, 32(9), pp. 1637–1641 (1986).
Ngo, *Int. J. Biochem.* 15(5), pp. 583–590 (1983).

*Primary Examiner*—Patricia A. Duffy

[57] ABSTRACT

Specific binding ligands can be detected with an assay which utilizes an immobilized receptor for the ligand, an immobilized reporter enzyme, an inhibitor antibody and a a water-soluble conjugate of the ligand and an anti-inhibitor antibody. Both antibodies are specific for the reporter enzyme, but the antibodies affect enzymatic activity differently. The inhibitor antibody effectively shuts down the activity of the reporter enzyme when it is complexed thereto. The anti-inhibitor antibody binds to the reporter enzyme, does not affect the enzymatic activity, but prevents the binding of the inhibitor enzyme. This assay provides a direct correlation of the generated signal to the target specific binding ligand.

9 Claims, 4 Drawing Sheets

SPECIFIC BINDING ASSAY USING ENZYME INHIBITOR AND ANTI-INHIBITOR ANTIBODIES

This is a continuation of application Ser. No. 08/250,980 filed May 31, 1994, now abandoned.

FIELD OF THE INVENTION

This invention relates to a specific binding assay using antibodies specific to enzymes which antibodies inhibit enzymatic activity. The assay also uses anti-inhibitor antibodies which are also specific to the same enzymes. This invention also relates to test kits useful in carrying out these assays. One utility of the invention is in diagnostics to detect various specific binding ligands which may be indicators of disease.

BACKGROUND OF THE INVENTION

There is a continuing need in medical practice and research, and in analytical and diagnostic procedures, for rapid and accurate determinations of chemical and biological substances present in various fluids, such as biological fluids. For example, the presence of drugs, narcotics, hormones, proteins, toxins, microorganisms, viruses, steroids or nucleic acids must be rapidly and accurately detected for effective research, diagnosis or treatment of various diseases or conditions.

Prostaglandin $E_2$ ($PGE_2$) is a potent biochemical mediator of inflammation in the body. Elevated levels of $PGE_2$ in crevicular fluid have been shown to be an indicator of periodontal disease. Due to the cyclical nature of periodontal diseases, an accurate measure of disease activity would be useful to determine periods of disease exacerbation and to aid in favorable disease treatment. If $PGE_2$ can be detected at very low concentrations (100 nmolar or less), the clinical usefulness of $PGE_2$ as an indicator of periodontal disease is optimized.

A wide variety of analytical methods have been developed in recent decades to detect various chemical or biological substances. Most of such methods rely on what are known in the art as "specific binding" reactions in which an unknown substance to be detected (known as a "specific binding ligand") reacts specifically and preferentially with a corresponding "receptor" molecule. Most well known specific binding reactions occur between immunoreactants, such as antibodies and antigens (foreign substances which produce immunological responses), but other specific binding reactions (such as avidin with biotin or a sugar with a lectin) are also known.

Many of the assay formats known in the art require one or more of the reactants to be immobilized on a solid substrate so that nonimmobilized reactants can be separated from immobilized reactants. "Sandwich" and "direct binding assays" are some of the assay formats which have been used in the art which require separation steps.

The standard immunological techniques, however, are more difficult to use with success in the detection of low molecular weight target specific binding ligands, such as $PGE_2$. It is particularly desirable to detect low concentrations (100 nmolar or less) of such ligands, but the standard immunological techniques are not always dependable for this purpose.

Quantification of low molecular weight target specific binding ligands generally involves a competition between unlabeled ligand (in a test sample) and labeled ligand for the binding sites of a receptor for the ligand. This is a typical competitive specific binding assay. Ligand in the test sample displaces labeled ligand from the receptor, and the amount of displacement is quantified by various methods. This results in an inverse correlation between the amount of bound ligand and the generated signal. Measurement of unbound ligand will yield a positive correlation.

Generally, the signal from bound ligand is easier to measure, but the signal is more difficult to interpret by health practitioners where there is a lack of sophisticated diagnostic training and equipment (for example, in doctors' offices).

Another problem with standard competitive specific binding assays is that the measurement of the free or bound labeled ligand is limited by the efficiency of the separation of free and bound molecules. If the free labeled ligand is not successfully separated from the bound labeled ligand, the sensitivity and specificity of the assay will be adversely affected.

Thus, there is a need for a sensitive specific binding assay in which efficient separation of free and bound labeled ligand is achieved to rapidly and easily detect low concentrations of various target specific binding ligands (especially those of low molecular weight).

SUMMARY OF THE INVENTION

The problems noted above have been solved with a specific binding method for the detection of a target specific binding ligand comprising the steps of:

A) bringing together, in any order:
1) a fluid sample suspected of containing a target specific binding ligand,
2) an immobilized receptor for the target specific binding ligand, and
3) a water-soluble conjugate of the target specific binding ligand and an anti-inhibitor antibody, the anti-inhibitor antibody having the following characteristics:
   a) specific to a reporter enzyme,
   b) a dissociation constant less than or equal to 100 nmolar, and
   c) binds to the reporter enzyme in such a manner that the enzymatic activity of the reporter enzyme is diminished by no more than about 20%, and binding of an inhibitor antibody specific to the reporter enzyme is substantially blocked, to form a water-insoluble complex between the immobilized receptor and either the target specific binding ligand or the water-soluble conjugate, B) separating the water-insoluble complex formed in step A) from a supernatant containing any uncomplexed water-soluble conjugate, C) bringing together, in any order:
   (i) a sample of the supernatant containing any uncomplexed water-soluble conjugate,
   (ii) an immobilized form of the reporter enzyme, and
   (iii) an inhibitor antibody having the following characteristics:
      a) specific to the reporter enzyme,
      b) a dissociation constant less than or equal to 125 nmolar, and
      c) binds to the reporter enzyme in such a manner as to inhibit the enzymatic activity of the reporter enzyme by at least about 80%, to form a water-insoluble complex between the immobilized reporter enzyme and either the uncomplexed water-soluble conjugate or the inhibitor antibody, and D) detecting any signal generated from the immobilized reporter enzyme as a determination of the target specific binding ligand in the fluid sample.

This invention also provides a test kit useful for the detection of a target specific binding ligand comprising, in individual packaging:

an immobilized receptor for the target specific binding ligand, and at least one additional reagent selected from the group consisting of:

a water-soluble conjugate of the target specific binding ligand and an anti-inhibitor antibody, the anti-inhibitor antibody having the following characteristics:
   a) specific to a reporter enzyme,
   b) a dissociation constant greater than or equal to 100 nmolar, and
   c) binds to the reporter enzyme in such a manner that the enzymatic activity of the reporter enzyme is diminished by no more than about 20%, and binding of any inhibitor antibody specific to the reporter enzyme is substantially blocked, an immobilized form of the reporter enzyme, and an inhibitor antibody having the following characteristics:
   a) specific to the reporter enzyme,
   b) a dissociation constant less than or equal to 125 nmolar, and
   c) binds to the reporter enzyme in such a manner as to inhibit the enzymatic activity of the reporter enzyme by at least about 80%.

The assay of this invention is predicated on the mutually exclusive binding of two different antibodies which are both specific to a reporter enzyme which is used as a signal generating reagent in the assay. One antibody (known herein as an "inhibitor" antibody) inhibits the enzymatic activity when it binds to the reporter enzyme. The other antibody (known herein as an "anti-inhibitor" antibody) binds to the reporter enzyme without inhibiting enzymatic activity to a significant extent. Yet, when bound to the receptor enzyme, the anti-inhibitor antibody prevents the inhibitor antibody from binding to the reporter enzyme.

The present invention is a specific binding assay in which the signal from the activity of the reporter enzyme is directly proportional to the amount of target specific binding ligand in the assay system. Free labeled ligand is measured in a suitable test device after a step to separate free and bound labeled ligand is carried out. This separation step improves the sensitivity of the assay without the need for a conventional wash step.

The assay of this invention provides for the rapid and easy detection of low concentrations of target specific binding ligands, especially low molecular weight ligands such as $PGE_2$. Thus, the assay can be used to advantage in the diagnosis or treatment of periodontal diseases.

DETAILED DESCRIPTION OF THE INVENTION

Definitions

The present invention can be used to qualitatively, quantitatively or semi-quantitatively detect any of a wide variety of target specific binding ligands (identified as ligands hereinafter) for which receptor molecules are available or manufacturable. Examples of ligand-receptor complexes (that is, a reaction product of ligand and corresponding receptor) include, but are not limited to, antibody-antigen, antibody-hapten, avidin-biotin, sugar-lectin, gelatin-fibronectin and Protein A-IgG complexes. For the purposes of this invention, complementary nucleic acids (that is, hybridized products of complementary strands) are also considered ligand-receptor complexes. Such complementary nucleic acids need not be complementary at every base pair. One strand can be longer than the other, or one strand can have a plurality of shorter complementary strands.

Ligands include, but are not limited to, peptides, polypeptides, proteins (including enzymes, antibodies, antigenic proteins, glycoproteins, lipoproteins and avidin), hormones (such as human chorionic gonadotropin, thyroxine, triiodothyronine, estrogen, ACTH and substance P), immune system modulators (such as interleukin-1, interleukin-6 and tumor necrosis factor α), vitamins, steroids, carbohydrates (such as polysaccharides), glycolipids, drugs (such as digoxin, diphenylhydantoin, phenobarbital, morphine, carbamazepine and theophylline), antibiotics (such as gentamicin), components of cells and viruses (such as Streptococcal species, herpes viruses, Gonococcal species, Chlamydial species, retroviruses, influenza viruses, Prevotella species, Porphyromonas species, Actinobacillus species and Mycobacterium species), nucleic acids (including single- and double-stranded oligonucleotides), pharmaceuticals, haptens, lectins, biotin, and other materials readily apparent to one skilled in the art.

In preferred embodiments, the ligands are antigenic substances (such as the drugs noted above) or antibodies (including anti-antibodies).

This invention is particularly useful for the detection of low molecular weight target specific binding ligands. By "low molecular weight target specific binding ligands" is meant compounds having a molecular weight of less than 500 daltons and which are capable of complexing with only a single corresponding receptor molecule (either because of only a single epitopic binding site, or because of steric hindrances). Such ligands include, but are not limited to, $PGE_2$ and other arachidonic acid metabolites, digoxin, diphenylhydantoin, carbamazepine, phenobarbital and other materials which would be readily apparent in the art. In a most preferred embodiment, this invention is useful for the efficient and rapid detection of $PGE_2$.

As used herein (unless otherwise noted), the term "antibody" includes whole immunoglobulin molecules having a single specificity as is conventional in the art. In addition, the term is intended to include chemically prepared fragments [such as Fab, F(ab)', F(ab)$_2$ fragments] of such molecules and genetically prepared equivalents thereof (such as "single chain antibody fragments" or ScFv fragments). Each type of antibodies described herein can be monoclonal or polyclonal.

Monoclonal antibodies include those molecules generally prepared using conventional hybridoma technology, but they can also be prepared by electrofusion, viral transformation and other procedures known in the art.

Preferably the monoclonal antibodies used in the invention are prepared by immunizing a suitable mammal (such as a mouse or rat) with the reporter enzyme (or the enzyme conjugated to carrier proteins), following the conventional procedures described by Kohler et al, *Nature* 256, 495 (1975).

A population of splenocytes from the immunized animals can be fused with suitable myeloma cell lines in the presence of polyethylene glycol (PEG1450) or another fusogen following the teaching of Lane [*J. Immunol. Methods* 81, pages 223–228 (1985)]. The resulting hybridized cells are diluted into selective media, distributed into microtiter plates and cultured for 7 to 21 days before screening to see what type of properties the antibodies possess. A specific procedure for preparing the antibodies is illustrated below.

A variety of myeloma cell lines are commercially available for hybridization with the mammal spleen cells. Sources of such cell lines include the American Type Culture Collection (ATCC) in Rockville, Md. Particularly useful myeloma cell lines include Sp2/0-Ag14 and P3x63Ag8 myeloma cells, both available from the ATCC. The first cell line is preferred.

In the preparation of monoclonal antibodies for use in this invention, selected hybridomas were cloned in soft agar and individual clones were plucked, cultured using conventional means and screened using the procedures described above. Monoclonal antibodies can be grown in shaker flasks or hollow fiber bioreactors, and collected and purified using conventional affinity chromatography on either immobilized Protein A or Protein G. Other conventional purification procedures can be used if desired.

Assay Protocol

In general, the assay protocol of this invention comprises bringing together the following reagents in any order:

1) the ligand (such as an antigenic substance) in a fluid sample of some type,
2) an immobilized receptor (such as an antibody) which is specific to and reactive with the ligand in the fluid sample, and
3) a water-soluble conjugate of the ligand (such as a drug) and an anti-inhibitor antibody which is specific to the reporter enzyme and has additional properties as defined below.

While these reagents can be brought together in any order, it is preferred that the ligand (fluid sample) and the immobilized receptor be mixed prior to contact with the water-soluble conjugate.

Once these reagents are brought together, appropriate reactions occur. Specifically, the ligand and water-soluble conjugate compete for available sites on the immobilized receptor, thereby forming water-insoluble specific binding complexes with the immobilized receptor.

The water-insoluble complex thus formed is then separated from uncomplexed water-soluble conjugate in a resulting supernatant. Separation means are described in more detail below.

Once separation is accomplished, a sample of the supernatant containing any uncomplexed water-soluble conjugate is brought together with the following, in any order:

1) an immobilized form of the reporter enzyme, and
2) an inhibitor antibody which is specific to the reporter enzyme and has additional characteristics which are described below.

While the reagents can be brought together in any order, it is preferred that the uncomplexed water-soluble conjugate and the immobilized form of the reporter enzyme be mixed prior to contact with the inhibitor antibody.

The result of this contact is a reaction product of water-soluble conjugate, inhibitor antibody or both with immobilized reporter enzyme. The amount of bound reaction product determines the level of enzymatic activity. Signal is then generated from the presence of the active reporter enzyme in direct proportion to the amount of ligand in the fluid sample using appropriate signal generating reagents (described below).

Thus, when no ligand is present in the original fluid sample, there will be no detectable water-soluble conjugate present in the supernatant after the separation step. When no detectable water-soluble conjugate is present in the supernatant, inhibitor antibody will complex with the immobilized reporter enzyme and prevent signal generation. When ligand is present in the fluid sample, water-soluble conjugate will be present in the supernatant. This conjugate complexes with the immobilized reporter enzyme, thereby preventing complexation with the inhibitor antibody. The reporter enzyme retains activity which is used to provide a detectable signal in direct proportion to the amount of ligand in the fluid sample.

In the various steps described above, the reagents noted above can be brought together at suitable temperature, generally in the range of from about 10 to about 35° C., and preferably at room temperature. The time for mixing can vary from a few seconds to 120 minutes, although typically the mixing step requires less than about five minutes. Preferably, the entire method is carried out within about 20 minutes.

The ligand to be detected may be present in any of a wide variety of fluid samples (or aqueous solutions) of animal or human body fluids, tissues or waste products including, but not limited to, whole blood, serum, plasma, lymph fluid, bile, urine, spinal fluid, lacrimal fluid, swab specimens, stool specimens, semen, vaginal secretions, saliva, tears, crevicular fluid, and others readily apparent to one skilled in the art. The size of the fluid sample can vary widely as is known in the art, but typically it is at least 1–10 $\mu$l.

The receptor is made available for reaction with the ligand or the ligand-anti-inhibitor antibody conjugate. Generally, such receptors are antibodies specific to the ligand.

The receptor is provided in immobilized form on a suitable water insoluble support. Suitable supports include, but are not limited to, polymeric, magnetic or glass particles, polymeric or glass filtration membranes, cellulosic filter papers, polymeric films, glass slides, test tubes, magnetic ferrofluids, test wells of test devices or microtiter plates or other materials readily apparent to one skilled in the art. Preferably, the receptor is immobilized on polymeric particles designed for this purpose, which particles are well known in the art. Reactive groups on the surface of particles include, but are not limited to, carboxy, 2-substituted ethylsulfonyl, vinylsulfonyl, epoxy, aldehyde, active halo atoms, amino, hydrazine and active esters such as succinimidoxycarbonyl.

Particularly useful particulate supports are described, for example in EP-A-0 323 692 (published Jul. 12, 1989) and U.S. Pat. No. 4,997,772 (Sutton et al) which are prepared from one or more ethylenically unsaturated polymerizable monomers having active halo atoms, activated 2-substituted ethylsulfonyl or vinylsulfonyl groups. Particularly useful carboxy-containing polymeric particles are described in U.S. Pat. No. 5,262,297 (Sutton et al), incorporated herein by reference. Other carboxy-containing polymeric particles are described in the art and many are commercially available.

Attachment of the receptor to the support can be accomplished using any of a variety of conventional procedures, such as coating to adsorb the receptor molecules or incubating to allow covalent reaction with reactive groups on the support. Such procedures are described, for example, in U.S. Pat. No. 5,252,457 (Snodgrass et al) and U.S. Pat. No. 5,262,297 (Sutton et al), both incorporated herein by reference, and references cited therein. The receptor can also be bound to supports having linking groups attached thereto, and such linking groups can be chemical moieties extending from the support or biological linking moieties such as peptides or antibodies to which the receptors can be complexed.

The amount of immobilized receptor useful in an assay would be readily apparent to a skilled worker from known assay protocols.

Reporter enzymes useful in this invention are enzymes which are typically used as labels in diagnostic methods. They include, but are not limited to a peroxidase, glucose oxidase, β-galactosidase, urease, alkaline phosphatase, creatine kinase, uricase, glucose-6-phosphate dehydrogenase and others readily apparent to one skilled in the art. A peroxidase (from any of various sources) is preferred, and horseradish peroxidase is most preferred.

The amount of reporter enzyme used in the assay is generally greater than or equal to about $10^{-11}$ molar so that background is negligible and kinetics for complex formation are acceptable. In addition, the amount is generally less than or equal to about $3 \times 10^{-8}$ molar so that enzyme substrates for producing signal are not reacted too quickly. Moreover, in preferred embodiments, the amount is less than the concentration of either the inhibitor or anti-inhibitor antibodies (described below).

The reporter enzyme is used in an immobilized form on a suitable support, similar to the receptor molecules. Thus, the teaching above relating to supports for receptor molecules applies equally for the reporter enzyme. Preferably, the reporter enzyme is immobilized on suitable polymeric particles by complexation with "binder" antibodies which are specific to the reporter enzyme. These binder antibodies have been adsorbed or covalently bound to the support using procedures similar to those described above for attaching the receptor molecules to such supports. In such embodiments, the binder antibodies act as linking groups between the support and the reporter enzyme molecules. Useful binder antibodies are described in more detail below. They do not appreciably inhibit the activity of the reporter enzyme, nor do they prevent binding of the inhibitor or anti-inhibitor antibodies to the reporter enzyme.

The inhibitor antibodies critical to the practice of this invention are specific to the reporter enzyme used in the assay. In addition, they have dissociation constants ($K_d$) less than or equal to 125 nmolar, and bind to the reporter enzyme in such a manner as to inhibit the enzymatic activity of the reporter enzyme by at least about 80% (preferably by at least about 95%, and more preferably by at least about 99%).

Screening for antibody production is a critical step in hybridoma technology. The hybridoma culture supernatants described above can be screened by three independent assays. The first assay enables one to choose antibodies which are specific to the reporter enzyme. The second and third assays can be used to determine which of the specific antibodies have enzyme inhibitory or anti-inhibitory activity (defined below). Screening for horseradish peroxidase specificity is described below as illustrative of how such a screening process would be carried out for a given reporter enzyme, but this invention is not to be construed as so limited. It is believed that antibodies to other reporter enzymes could be similarly prepared and identified. Screening for specificity to the reporter enzyme can be readily accomplished using conventional Enzyme Linked Immunosorbent Assays (ELISA) in polystyrene microtiter plates containing adsorbed horseradish peroxidase conjugate.

Specificity for Horseradish Peroxidase

A sample (50 μl/plate well) of each culture supernate is placed in a microtiter well coated with a conjugate of horseradish peroxidase and an irrelevant antibody which served to mediate the adsorption of horseradish peroxidase to the microtiter plate. This antibody can be obtained, for example, from Jackson Immunoresearch. After a 30–60 minute incubation, the plates are washed with a suitable buffered solution of a nonionic surfactant, and the presence of mouse or rat horseradish peroxidase specific monoclonal antibodies is detected with a conjugate of anti-mouse IgG or anti-rat IgG and alkaline phosphatase (conjugate with anti-mouse Fc obtained from, for example, Jackson Immunoresearch). A dye signal can be generated by adding the substrate o-nitrophenyl phosphate disodium salt (4 mg/ml) in tris(hydroxymethyl)aminomethane buffer (1.5 molar, pH 8). Other signal producing reagents, or enzyme labels can be similarly used. The screened antibodies which provide a dye signal after about 30 minutes of at least twice as dense as a background signal are considered to be specific for horseradish peroxidase. The dye signal can be measured using a conventional microtiter plate reader or spectrophotometer.

Antibodies specific to horseradish peroxidase can be screened for inhibitory function as follows:

Assay for Enzyme Inhibition

A sample (50 μl) of each culture supernate is placed in a microtiter plate well, followed by addition of a solution (50 μl) of horseradish peroxidase (0.2 nmolar) and gelatin (0.8%) in phosphate buffered saline, and the resulting mixtures are allowed to stand for 10 minutes at room temperature. Residual enzyme activity is then determined by adding 100 μl of the horseradish peroxidase substrate, o-phenylenediamine (1 mg/ml) in citrate/phosphate buffer (50 mmolar, pH 5.5), and measuring the amount of dye signal at 450 nm using a conventional spectrophotometer (rate of 100 mOD/minute). Other substrates, or dye providing reagents can be similarly used.

Those culture supernates that inhibit horseradish peroxidase by more than 20% (compared to a control without the presence of monoclonal antibody) are considered for further investigation as inhibitor antibodies.

The antibodies evaluated in this manner are subjected to further evaluation to find those which are within the scope of the present invention, namely those that inhibit the reporter enzyme (such as horseradish peroxidase) activity by at least about 80%. Preferably, the amount of inhibition is at least about 95%, and more preferably at least about 99%. The evaluation for inhibition was carried out by the procedure described above.

Antibodies specific to the reporter enzyme (such as horseradish peroxidase) are also screened for their ability to inhibit the binding of inhibitor antibodies to the reporter enzyme. A representative screening process for anti-inhibitor antibodies specific to horseradish peroxidase is described below. This invention is not to be construed as so limited.

Assay for Anti-Inhibition

A sample (25 μl) of horseradish peroxidase (0.4 nmolar) is added to each well of a microtiter plate, followed by addition of a sample (50 μl) of each culture supernate, incubated 30 minutes, followed by addition of the inhibitor monoclonal antibody 4-22.2 (25 μl, 15 nmolar, defined below in Table I). After a 10 minute incubation, substrate solution (100 μl) is added and the dye signal from peroxidase activity is evaluated as described above (that is, using o-phenylenediamine as the substrate). Anti-inhibitor antibodies within the scope of this invention are defined as those which block the inhibition of horseradish peroxidase activity by the inhibitor antibody 4-22.2 described herein. Generally, the inhibitor antibody is added at a level sufficient to inhibit 80–90% of enzymatic activity.

When used to modify the percent of enzymatic activity inhibition in this disclosure and the claims, the term "about" refers to a variation of ±5%. When used to modify the $K_d$ values herein, the term "about" refers to a variation of ±50%.

The dissociation constants ($K_d$) for inhibitor antibodies were determined by measuring the concentration of the antibody required to inhibit 50% of reporter enzyme (such as horseradish peroxidase) activity (as compared to enzymatic activity in the absence of antibody). The inhibitor antibodies described herein generally have a $K_d$ less than or equal to 125 nmolar, preferably a $K_d$ less than or equal to 50 nmolar, and more preferably a $K_d$ less than or equal to 1 nmolar.

The $K_d$ values for anti-inhibitor antibodies were determined by measuring the concentration of antibody required to prevent 50% of the inhibition of 0.1 nmolar horseradish peroxidase by 10 nmolar of inhibitor antibody 4-22.2 (defined below in Table I) which was determined to inhibit about 99% of the enzymatic activity as defined above. These $K_d$ values are generally less than or equal to about 50 nmolar, preferably less than or equal to about 25 nmolar and more preferably less than or equal to about 5 nmolar. The lower the $K_d$ value of the antibody, the lower the detection limit for the ligand. Preferably, these antibodies diminish the activity of horseradish peroxidase by no more than about 6%.

It should be understood that these $K_d$ values are relative measures for the antibodies, and that alternative methods for measuring that parameter may give higher or lower values.

The inhibitor, anti-inhibitor and binder monoclonal antibodies used in the practice of this invention can be of any useful class, for example, IgA, IgE, IgM or IgG. Preferably, they are of the IgG class. Determination of isotype of cloned antibody cultures is achieved by using conventional isotyping assays and test kits which are commercially available. Reporter enzymes, such as horseradish peroxidase can be immobilized on various supports, directly or indirectly, for isotyping assays.

The following Table I lists useful inhibitor monoclonal antibodies by species, isotype, $K_d$ and maximum horseradish peroxidase inhibition:

TABLE I

| Antibody | Species/Isotype | Kd (nmolar) | Max. Inhibition (%) |
|---|---|---|---|
| 4-22.2 | rat*/IgG1 | 0.14 | 99 |
| 3-8.1 | mouse**/IgG2a | 25 | 97 |
| 2-3.1 | mouse**/IgG1 | 2 | 85 |
| 3-7.2 | mouse**/IgG2a | 10 | 85 |
| 4-4.3 | rat*/IgG2a | 20 | 82 |
| 3-3.1 | mouse**/IgG1 | 50 | 93 |
| 3-6.2 | mouse**/IgG2a | 63 | 94 |
| 3-2.2 | mouse**/IgG2a | 110 | 91 |

*Sprague-Dawley rats
**Swiss/Webster mice

The 4-22.2 monoclonal antibody is preferred. It is prepared using the novel hybridoma cell line identified herein as HB 11603 which has been deposited with the ATCC.

The following Table II lists useful anti-inhibitor monoclonal antibodies useful in the practice of this invention by species, isotype, Kd and maximum horseradish peroxidase inhibition:

TABLE II

| Antibody | Species/Isotype | Kd (nmolar) | Max. Inhibition (%) |
|---|---|---|---|
| 7-32.2 | mouse**/IgG2a | 3.3 | 0 |
| 6-89.1 | rat*/IgG2a | 3.5 | 6 |
| 6-82.1 | rat*/IgG2a | 7.0 | 10 |
| 6-71.2 | rat*/IgG2a | 10 | 8 |
| 6-55.2 | rat*/IgG1 | 20 | 6 |

*Sprague-Dawley rats
**$CAF_1$ mice

The 6-89.1 and 7-32.2 monoclonal antibodies are preferred. They are prepared using the novel hybridoma cell lines identified herein as HB 11635 and HB 11604, respectively, which have been deposited with the ATCC under the Budapest Treaty. The 7-32.2 monoclonal antibodies are most preferred.

The amount of inhibitor antibody used in the method of this invention is generally whatever amount is needed to inhibit enzyme activity at least about 80%. Generally, this is from about $10^{-9}$ to about $10^{-5}$ molar, with an amount of from about $10^{-7}$ to about $10^{-6}$ molar being preferred. The amount of inhibitor antibody will vary depending upon the level of inhibition of enzymatic activity that is desired, and the inhibition properties of a given antibody.

Also used in the method of this invention are water-soluble conjugates of the ligand and an anti-inhibitor antibody. The conjugates can be prepared using any conventional technique of the art for covalently binding proteins, hormones, drugs or other chemical or biological compounds having requisite reactive groups. Thus, the various reactive groups of the antibodies and ligand can be considered in choosing the means for making the conjugate, such groups including, but are not limited to, carboxy, amino, hydroxy, thiol and imidazole groups. Useful methods of binding include, but are not limited to, binding of peptides, periodate oxidation, use of glutaraldehyde, dication ethers, carbamoylonium salts, carbodiimides or N-hydroxysuccinide, and others readily apparent to one skilled in the art. Details for each of these and other methods are found in voluminous literature, including Williams et al *Methods in Immunology and Immunochemistry*, Academic Press, New York, 1976, and Yoshitake et al, *Eur. J. Biochem.* 101, 395 (1979). It is to be understood that such conjugates are often prepared using derivatives or analogs (also known as haptens) of the ligand to be detected, such derivatives having reactive groups or linking moieties which may be desirable for binding the hapten to the reporter enzyme. Specific details of the preparation of several conjugates are provided below prior to the examples.

The amount of water-soluble conjugate used in the method of this invention is generally that amount needed to inhibit enzymatic activity by no more than about 20%, and to block substantially all reaction of inhibitor antibody with the reporter enzyme. By "substantially all" is meant at least 95%. Typically, the amount of conjugate is from about $10^{11}$ to about $10^{-7}$ molar, with amounts of from about $5 \times 10^{-10}$ to about $10^{-8}$ molar being preferred. The amount will vary depending upon properties of a given antibody, the amount of enzymatic activity desired and the amount of inhibitor antibody to be blocked.

In the screening procedure described above, binder antibodies can also be identified. Such antibodies can be used to bind reporter enzymes to water-insoluble supports. These antibodies are specific for the reporter enzyme of interest, generally have dissociation constants less than or equal to 100 nmolar, and bind to the reporter enzyme in such a manner as to diminish the enzymatic activity by less than about 20%. They do not exhibit significant inhibitory or anti-inhibitory properties compared to the inhibitor and anti-inhibitor antibodies described above. A particularly useful binder antibody is identified herein as "5-10" and is an IgG1 antibody derived using the procedures described above using A/J mice. Its $K_d$ was determined to be $10^{-8}$ and its inhibition of horseradish peroxidase was less than 1%.

Signal generated by the reporter enzyme in the course of the assay of this invention can be a chemiluminescent, electrochemical or colorimetric signal depending upon the particular reporter enzyme and corresponding reagents (such as substrates) used to generate the signal.

Chemiluminescent signals can be generated in a wide variety of ways in response to a reporter enzyme. In most chemiluminescent systems, the reporter enzyme is a peroxidase, and an oxidant such as hydrogen peroxide is present or generated in some fashion (for example, the reaction of an oxidase with its substrate). Useful chemiluminescent signals are generated using, for example, acridinium salts, tetrakis(dimethylamino)ethylene, luciferin, lucigenin, oxalyl chloride, certain oxidases (for example, xanthine oxidase) and 2,3-dihydro-1,4-phthalazinediones (such as luminol and isoluminol). Many examples of such compounds and their uses are known in the art, for example, in U.S. Pat. No. 4,383,031 (Boguslaski et al), U.S. Pat. No. 4,598,044 (Kricka et al), U.S. Pat. No. 4,729,950 (Kricka et al), U.S. Pat. No. 5,108,893 (Baret) and *Chemiluminescence in Organic Chemistry* (Gundermann et al, Springer-Verlag, Berlin, 1987, pages 204–207). Where a chemiluminescent signal is generated, preferably peroxidase is used as the reporter enzyme, and luminol or a similar compound is used as a signal generating reagent.

Preferably, a calorimetric signal is generated in the method of this invention. Such signals can be achieved using a wide variety of reporter enzymes and reagents, as is well known in the art. Where the reporter enzyme is a peroxidase, as is preferred, useful dye-providing reagents include, but are not limited to, tetramethylbenzidine and derivatives thereof, o-phenylenediamine, triarylmethanes, and imidazole leuco dyes, such as the triarylimidazole leuco dyes described in U.S. Pat. No. 4,087,747 (Bruschi) and U.S. Pat. No. 5,024,935 (McClune), both incorporated herein by reference. Substrate solutions for the various reporter enzymes can be provided at any suitable time in the assay of this invention, or they can be present throughout the entire assay. One useful substrate solution for the triarylimidazole leuco dyes includes hydrogen peroxide, and an electron transfer agent such as 4'-hydroxyacetanilide or 3'-chloro-4'-hydroxyacetanilide in a suitable buffer.

The amount of various reagents needed to produce a desired signal would be readily apparent to one skilled in the art from consulting the voluminous literature available for the various signal producing systems. Specific enablement for a preferred calorimetric system is shown below in the examples.

The equipment needed for detecting the desired signal generated in the assay also would be readily apparent to one skilled in the art. Some colorimetric signals could be readily evaluated from the user's visual observations, but more generally, the signals are evaluated using appropriate apparatus for receiving and evaluating calorimetric, fluorimetric or chemiluminescent signals.

In step B) of the present invention, described above, the water-insoluble complex between immobilized receptor and either the ligand or water-soluble conjugate is separated from uncomplexed materials (including uncomplexed water-soluble conjugate) using any suitable equipment and procedure. For example, the reaction mixture from step A) can be filtered using any of a variety of filter materials which will let supernatant (containing water-soluble materials) pass through while retaining the water-insoluble complex. Alternatively, the supernatant can be decanted from the water-insoluble complex which may be attached to a microtiter plate, test tube or other solid device. Preferably, the water-insoluble complex is attached to particles of a suitable material (such as polymeric particles as described above), and such particles are readily filtered or centrifuged.

Useful filtration devices would be readily apparent to one skilled in the art. Preferred filtration devices are described in U.S. Pat. No. 4,948,561 (Hinckley et al, FIG. 1).

A most preferred filtration device contains a microporous filtration membrane having an average pore size of from about 0.5 to about 10 μm. Such membranes are commercially available as LOPRODYNE™ membranes from Pall Corp.

Step C) and following steps in the method of this invention can be carried out in a suitable container wherein immobilized reporter enzyme, inhibitor antibodies and supernatant can be suitably mixed. For example, this mixing can be carried out in microtiter plates, test tubes, microfuge tubes and other devices readily apparent to one skilled in the art. Preferably, the method is carried out in disposable test devices in which the reporter enzyme is immobilized in a suitable fashion. Such test devices would be readily apparent to one skilled in the art and would include such devices as are described in U.S. Pat. No. 3,825,410 (Bagshawe), U.S. Pat. No. 3,888,629 (Bagshawe), U.S. Pat. No. 3,970,429 (Updike), U.S. Pat. No. 4,446,232 (Liotta), U.S. Pat. No. 4,833,087 (Hinckley), U.S. Pat. No. 4,877,586 (Devaney, Jr. et al), U.S. Pat. No. 4,921,677 (Hinckley et al), U.S. Pat. No. 4,923,680 (Nelson), U.S. Pat. No. 4,948,561 (Hinckley et al), U.S. Pat. No. 4,988,627 (Smith-Lewis) and U.S. Pat. No. 5,132,085 (Pelanek). The preferred test devices contain multiple test wells containing microporous filtration membranes (such as LOPRODYNE™ or BIODYNE™ membranes from Pall Corp.). Such devices are available from Eastman Kodak Company as SURECELL™ or EVAL-USITE™ Test kit disposable test devices. The immobilized reporter enzyme, if desired, can be disposed on the membranes prior to use in the method of this invention.

The reagents described herein and used in the practice of the method of this invention can be supplied as individually packaged components of a test kit. Such kits contain an immobilized receptor as described above, and at least one additional reagent selected from the water-soluble conjugates, immobilized reporter enzyme and inhibitor antibodies described above. In most embodiments, the test kits include all of these reagents as well as suitable signal producing reagents, containers, equipment and instructions for carrying out the method of the invention. For example, the test kits can also include a disposable test device (as described above), and a suitable filtration device (as described above).

The following examples are illustrative of the invention and not meant to be limiting. All percentages are by weight, unless otherwise indicated.

MATERIALS AND METHODS FOR EXAMPLES

Preparation of Inhibitor Monoclonal Antibody Specific to Horseradish Peroxidase

The monoclonal antibody identified above as 4-22.2 in Table I was prepared as follows:

Sprague-Dawley rats were injected with a solution of horseradish peroxidase (400 µg) in commercially available TDM/MPL emulsion adjuvant (RIBI Corporation) four times at four week intervals. A fifth injection was made with horseradish peroxidase (400 µg) in phosphate buffered saline solution. Three days later, splenocytes from the immunized rats were fused with cells from the Sp2/0-Ag14 myeloma cell line using conventional procedures.

Screening of the resulting antibodies for specificity to horseradish peroxidase was carried out as described above by adding 50 µl of the culture supernatant to the wells of a microtiter plate coated with a conjugate of horseradish peroxidase and irrelevant antibody which served to mediate the adsorption of the enzyme to the microtiter plate. The bound antibody was detected by adding a conjugate of alkaline phosphatase with goat anti-mouse IgG Fc (Jackson Immunoresearch), followed by signal generation using 4 mg/ml of p-nitrophenyl phosphate disodium salt (Sigma Chemical) as substrate for the alkaline phosphatase in tris (hydroxymethyl)aminomethane buffer (1.5 molar, pH 8). The dye signal was evaluated after 30 minutes using a conventional microtiter plate reader.

Screening for horseradish peroxidase inhibitory function was carried out by adding a sample (50 µl) of each culture supernatant to microtiter plate wells, followed by addition of horseradish peroxidase (0.2 nmolar) and gelatin (0.8%) in phosphate buffered saline solution, and the resulting mixtures were allowed to incubate for 10 minutes at room temperature. Residual horseradish peroxidase activity was determined by adding a solution (100 µl) of o-phenylenediamine (1 mg/ml) in citrate/phosphate buffer (50 µl, 50 mmolar, pH 5.5), and measuring the amount of dye signal at 450 nm using a conventional microtiter plate reader (100 mOD/minute).

Those antibodies which inhibited the enzymatic activity by at least 20% were selected by adding equal volumes of the culture supernatant and horseradish peroxidase to microtiter plate wells and using the procedure described above ("Assay for Enzyme Inhibition"). Antibody 4-22.2 was determined to inhibit horseradish peroxidase activity 99%.

Preparation of Anti-Inhibitor Monoclonal Antibody Specific to Horseradish Peroxidase The monoclonal antibody identified above as 7-32.2 in Table II was prepared as follows:

Immunization of rats and fusion of the resulting splenocytes were carried out as described above in the previous preparation. Mice were given four immunizations of a conjugate (100 µg/ml each) of horseradish peroxidase with C-reactive protein in TDM/MPL emulsion adjuvant over four week intervals. A fifth and final immunization in phosphate buffered saline solution was carried out. Screening for horseradish peroxidase activity was carried out as described above except that after the plates were shaken for 10–30 minutes, a solution (25 µl) of the inhibitor antibody 4-22.2 (about 15 nmolar, described above) was added to each plate well. The resulting mixtures were allowed to incubate for 10 minutes at room temperature.

Residual horseradish peroxidase activity was determined by adding a solution (100 µl) of o-phenylenediamine (1.2 mg/ml) in citrate/phosphate buffer (0.1 molar, pH 5.5), and measuring the amount of dye signal at 450 nm using a conventional spectrophotometer as described in the previous preparation.

The determination of an antibody which is an anti-inhibitor was carried out using the procedure described above ("Assay for Anti-Inhibition"). Antibody 7-32.2 was measured to diminish enzyme activity by less than 1% (essentially 0%).

The monoclonal antibody identified above as 6-89.1 in Table II was similarly prepared.

The inhibitor and anti-inhibitor antibodies described above were stored at 4° C. as separate stock solutions prior to use in assays. Each stock solution included about 1 mg of antibody per ml of phosphate buffered saline solution and 0.02% merthiolate preservative.

Preparation of Conjugates of Anti-Inhibitor Monoclonal Antibody and Diphenylhydantoin Hapten Water-soluble conjugates of a diphenylhydantoin hapten and two anti-inhibitor monoclonal antibodies were prepared. This preparation is representative only, and is not essential to preparing conjugates useful in the present invention. Alternative preparatory methods also exist.

The hapten, 5,5-diphenyl-3-{4-[4-(3-succinimidoxycarbonylpropionyl)-1-piperazinylcarbonyl]butyl}-2,4-imidazolidinedione, was prepared by procedures described in Preparatory Example 2 of EP-A-0 517 327 (published May 5, 1993).

This hapten was conjugated to the monoclonal antibodies identified as 7-32.2 or 6-89.1 (Table II) in either a 9:1 or 18:1 molar ratio by adding concentrated hapten in dimethyl sulfoxide slowly, dropwise to a solution of either antibody (1 mg/ml) in N-[2-hydroxyethyl]piperizine-N'-[3-propanesulfonic acid] buffer (0.1 molar, pH 8). The resulting mixtures were incubated at room temperature for 4 hours, then dialyzed overnight into phosphate buffered saline solution. The final product conjugates were filtered through a commercially available 0.22 µmeter filter (Nalge Corporation, Rochester, N.Y.). The final protein concentration was determined by absorbance at 280 nm using a commercially available spectrophotometer (Beckman Instruments).

Preparation of Conjugates of Anti-Inhibitor Monoclonal Antibody and Phenobarbital Hapten Two water-soluble conjugates of a phenobarbital hapten and anti-inhibitor monoclonal antibodies were prepared in the following manner. This preparation is representative only, and is not essential to preparing conjugates useful in the present invention. Alternative preparatory methods also exist.

The hapten, 5-ethyl-5-phenyl-1-{4-[4-(3-succinimidoxycarbonylpropionyl)-1-piperazinylcarbonyl]butyl}-2,4,6-(1H,3H,5H)pyrimidinetrione, was prepared by procedures described in Preparatory Example 4 of EP-A-0 517 327 (published May 5, 1993).

This hapten was conjugated to the monoclonal antibodies identified as 7-32.3 or 6-89.1 (Table II) in either a 9:1, 18:1 or 27:1 molar ratio by adding concentrated hapten in dimethyl sulfoxide slowly, dropwise to a solution of either antibody (1 mg/ml) in N-[2-hydroxyethyl]piperizine-N'-[3-propanesulfonic acid] buffer (0.1 molar, pH 8). The resulting mixtures were incubated at room temperature for 4 hours, then dialyzed overnight into phosphate buffered saline solution. The final product conjugates were filtered through a commercially available 0.22 $\mu$meter filter (Nalge Corporation, Rochester, N.Y.). The final protein concentration was determined by absorbance at 280 nm using a commercially available spectrophotometer (Beckman Instruments).

Preparation of Conjugates of Anti-Inhibitor Monoclonal Antibody and Digoxin Hapten Two water-soluble conjugates of a digoxin hapten and anti-inhibitor monoclonal antibodies was prepared in the following manner. This preparation is representative, as other methods for making such conjugates can be used.

Hapten was conjugated to the monoclonal antibodies identified as 7-32.3 or 6-89.1 (Table II) by diluting 2 mg of each antibody 1:1 with sodium acetate (0.1 molar, pH 5.5), not to exceed 2 ml. Sodium metaperiodate (1 ml) was added at 6.66 mg/ml. The reaction mixture was covered with foil and rotated for 20 minutes at room temperature. Excess sodium metaperiodate was removed by passing the reaction mixture over a commercially available PD10 column (Pharmacia, Inc.) and preequilibrated with sodium acetate (0.1 molar, pH 5.5). To vials (3 mg in 1 ml) of digoxigenin-x-hydrazide (Boehringer Mannheim) was added to each mixture and incubated for 1 hour at room temperature. To block reaction, excess glycine (final concentration of 10%) was added at pH 7, followed by sodium cyanoborohydride in water to a final concentration of 20 mmolar. The reaction mixture was stirred for 3 hours at room temperature, then dialyzed overnight into 3-(N-morpholino)propanesulfonic acid (0.02 molar, pH 7) buffer. The final product conjugates were filtered through a commercially available 0.22 $\mu$meter filter (Nalge Corporation, Rochester, N.Y.). The final protein concentration was determined by absorbance at 280 nm using a commercially available spectrophotometer (Beckman Instruments).

Preparation of Conjugate of Anti-Inhibitor Monoclonal Antibody and PGE$_2$

A water-soluble conjugate of PGE$_2$ and an anti-inhibitor monoclonal antibody of this invention, 7-32.2 (Table I above) was prepared in the following manner. This preparation is representative only, and is not essential to preparing conjugates of the present invention. Alternative preparatory methods also exist.

A solution of PGE$_2$ (0.94 mg, $1.67 \times 10^{-6}$ molar) in N,N-dimethylformamide (0.5 ml) was mixed with an equimolar amount of tributylamine (50 $\mu$l of a 1:100 solution in N,N-dimethylformamide), followed by mixing with an equimolar amount of isobutyl chloroformate (36.5 $\mu$l of a 1:100 solution in N,N-dimethylformamide). The resulting mixture was allowed to incubate on ice for 20 minutes, then added dropwise to a solution (2.5 ml) of monoclonal antibody 7-32.2 (2.5 mg/ml, Table II) in 3-(N-morpholino) propanesulfonic acid buffer (0.02 molar) which was adjusted to pH 9 with sodium hydroxide (0.05 molar) to provide 5 mg of antibody, and allowed to incubate at room temperature for 90 minutes. It was then mixed with hydroxylamine (0.433 ml, 0.2 molar, pH 7) to provide a final volume of 3.9 ml with a hydroxylamine concentration of 0.02 molar. The final mixture was allowed to incubate two hours at room temperature to complete formation of the conjugate, and dialyzed against 5 liters of phosphate buffered saline solution overnight. The dialyzed solution comprised 0.863 mg/ml (4.32 mg) of conjugate, as determined by conventional spectrophotometry.

Immobilization of Antibodies

Antibodies specific to various target specific binding ligands used in the assays of the examples were obtained and immobilized on particles of poly[styrene-co-p-(2-chloroethylsulfonylmethyl)styrene] (monomer weight ratio of 95:5, 1 $\mu$m average size) using the procedures described in U.S. Pat. No. 5,177,023 (Sutton et al), incorporated herein by reference. The resulting immobilized antibodies were washed and resuspended in N-[tris(hydroxymethyl)methyl]-2-aminoethanesulfonic acid buffer (0.1 molar, pH 7) for use in an assay.

Horseradish peroxidase, containing isoenzyme C, was obtained from Servac, Inc. (South Africa). It was immobilized on the same type of polymeric particles described above as follows. It should be understood, however, that any other carrier protein could be similar used to immobilize the enzyme to the particles.

A suspension (3% solids) of the particles were mixed with the binder anti-peroxidase antibody 1-21.1 (0.829 mg/ml) for 24 hours at room temperature in borate buffer (0.1 molar, pH 8.5). The resulting attached coverage of antibody on the particles was about 0.0124 g antibody per gram of particles. The immobilized anti-peroxidase antibodies were washed and resuspended in N-tris(hydroxymethyl)methyl-2-aminoethanesulfonic acid buffer (0.1 molar, pH 7). A suspension (1%) of the immobilized antibodies was then mixed with the horseradish peroxidase ($2.5 \times 10^{-8}$ molar) for about 2 hours at room temperature. The resulting reagent was washed and resuspended in 3-(N-morpholino) propanesulfonic acid buffer (0.2 molar, pH 7) containing bovine serum albumin (1%).

Solutions of water-soluble conjugates of ligand and anti-inhibitor antibodies were prepared and used in 3-(N-morpholino)propanesulfonic acid buffer (0.2 molar, pH 7) containing bovine serum albumin (1%). The amounts of conjugate in the respective solutions were as follows:

Diphenylhydantoin-antibody: $1 \times 10^{-9}$ molar,
PGE$_2$-antibody: $1 \times 10^{-9}$ molar,
Digoxin-antibody: $5 \times 10^{-9}$ molar, and
Phenobarbital-antibody: $5 \times 10^{-9}$ molar.

Unlabeled ligands used as target analytes were prepared for use in similar solutions at various concentrations.

Inhibitor antibody specific to horseradish peroxidase was used at $5 \times 10^{-7}$ molar in 3-(N-morpholino)propanesulfonic acid buffer (0.2 molar, pH 7) containing bovine serum albumin (1%).

Enzyme substrate solution was prepared by adding a solution (5 ml) of 4,5-bis(4-dimethylaminophenyl)-2-(4-hydroxy-3-methoxyphenyl)imidazole leuco dye (1 g) in N,N-dimethylformamide to a solution (500 ml) of polyvinylpyrrolidone (125 g) and stirred for an hour. Diethylenetriaminepentaacetic acid (1 ml, 0.1 molar) was added to a solution (9500 ml) of monobasic sodium phosphate monohydrate (13.8 g) with stirring, followed by addition of 3'-chloro-4'-hydroxyacetanilide (9.4 g). The resulting mixture was stirred to dissolve the components, and the pH was adjusted to 6.8 with 50% sodium hydroxide. With vigorous stirring, it was then mixed with the leuco dye solution. Hydrogen peroxide (10 ml, 30%) was added, and the final mixture was stirred another 15 minutes.

A dye signal stop solution contained benzohydroxamic acid (0.1%) and merthiolate (0.01%) in phosphate buffered saline (0.05 molar, pH 7.3).

Steps A) and B) of the method of the present invention were carried out using an extraction device containing a tube (6 ml volume) to which was fitted a filter cap which contains a LOPRODYNE™ microporous membrane (1.2 µm average pore size), as described in U.S. Pat. No. 4,948,561 (noted above).

Steps C) and D) of the present invention were carried out in disposable test devices from an EVALUSITE™ Test kit [like those described in U.S. Pat. No. 5,132,085 (Pelanek)], containing three test wells, each having a LOPRODYNE™ microporous membrane (1.2 µm average pore size). Onto the membrane of each well was applied and dried, a suspension (1.8 µl, 0.3% solids) of the immobilized horseradish peroxidase reagent described above.

EXAMPLE 1

Assay for Prostaglandin $PGE_2$

The ligand $PGE_2$ was determined according to the method of the present invention as follows.

To an extraction device was added, in order:

N-[tris(hydroxymethyl)methyl]-2-aminoethanesulfonic acid buffer (0.201 ml, 0.1 molar, pH 7), anti-$PGE_2$ antibody reagent (0.069 ml, 0.6% solids, final concentration), and unlabelled $PGE_2$ solution (0.03 ml, various ligand concentrations), followed by incubation for 5 minutes at room temperature. Water-soluble $PGE_2$-anti-inhibitor antibody conjugate (0.03 ml) was then added, followed by incubation for 5 minutes at room temperature. The filter cap was then placed on the tube.

Supernatant from the extraction tube was squeezed through the filter cap and applied to the test wells of the disposable test device containing the immobilized horseradish peroxidase reagent. Where target $PGE_2$ was present, the supernatant contained unbound water-soluble conjugate of $PGE_2$ and anti-inhibitor antibody.

After incubation for 5 minutes at room temperature, inhibitor antibody (100 µl) was added to the test wells, followed by another incubation for 5 minutes at room temperature. Three drops of the enzyme substrate solution were added. After incubation for 2 minutes at room temperature, the dye signal stop solution (3 drops) was added, and the resulting dye signal was evaluated.

Positive control assays were similarly carried out in the absence of target $PGE_2$ and immobilized anti-$PGE_2$ antibodies in the extraction device. In such situations, all of the water-soluble conjugate was free to complex with the peroxidase in the test device, providing the maximum dye signal.

Negative control assays were similarly carried out in the absence of target $PGE_2$, but with immobilized anti-$PGE_2$ antibodies present in the extraction device. The resulting dye signal was from background only.

Figure 1:
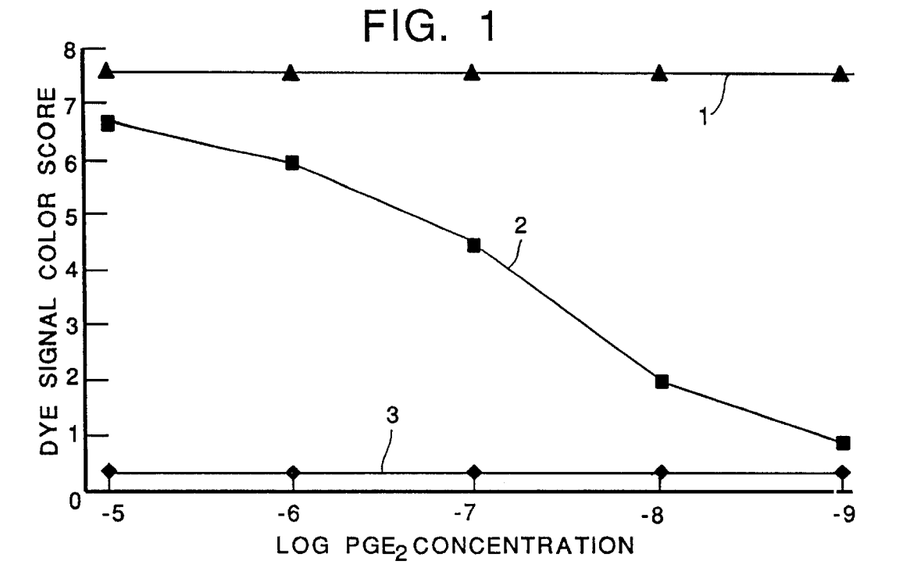
FIG. 1 is a graphical plot of dye signal color score versus log $PGE_2$ concentration and is described in more detail in Example 1 below.
Figure 2:
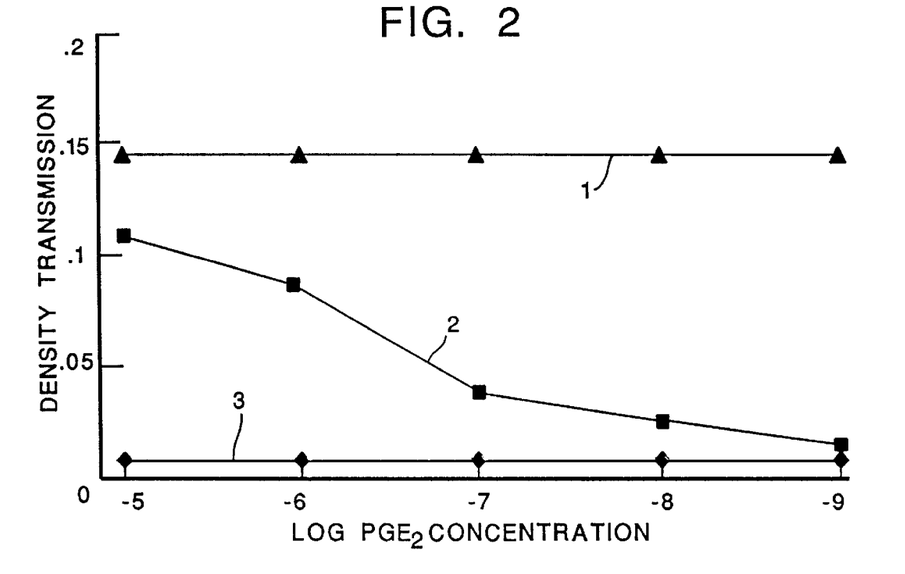
FIG. 2 is a graphical plot of dye signal density transmission versus log $PGE_2$ concentration and is described in more detail in Example 1 below.

A titration of dye signal above background was observed as a function of $PGE_2$ concentration with a detection limit of about $1 \times 10^{-9}$ molar $PGE_2$ (after 1:100 dilution) which is the minimum concentration for this analyte to be a marker for the presence of periodontal disease. FIGS. 1 and 2 show the results of these assays in the form of dose response curves, including the positive and negative controls (curves 1 and 3, respectively), and the assay of the invention (curve 2). In FIG. 1, dye signal (observed color score from a color density chart) is plotted on the y-axis and $PGE_2$ concentration [log ($PGE_2$)] is plotted on the x-axis. FIG. 2 is a similar plot but with dye signal (density transmission) plotted on the y-axis.

EXAMPLE 2

Assay for Diphenylhydantoin

The ligand diphenylhydantoin (phenytoin) was determined according to the method of the present invention as follows.

To an extraction device was added, in order:

N-[tris(hydroxymethyl)methyl]-2-aminoethanesulfonic acid buffer (0.211 ml, 0.1 molar, pH 7), anti-diphenylhydantoin antibody reagent (0.059 ml, 0.2% solids, final concentration), and unlabelled diphenylhydrantoin solution (0.03 ml, various ligand concentrations), followed by incubation for 5 minutes at room temperature. Water-soluble diphenylhydrantoin-anti-inhibitor antibody conjugate (0.03 ml) was then added, followed by incubation for 5 minutes at room temperature. The filter cap was then placed on the tube.

Supernatant from the extraction tube was squeezed through the filter cap and applied to the test wells of the disposable test device containing the immobilized horseradish peroxidase reagent. Where target diphenylhydantoin was present, the supernatant contained unbound water-soluble conjugate of diphenylhydantoin and anti-inhibitor antibody.

After incubation for 5 minutes at room temperature, inhibitor antibody (100 µl) was added to the test wells, followed by another incubation for 5 minutes at room temperature. Three drops of the enzyme substrate solution were added. After incubation for 2 minutes at room temperature, the dye signal stop solution (3 drops) was added, and the resulting dye signal was evaluated.

Positive and negative control assays were similarly carried out as described in Example 1.

Figure 3:
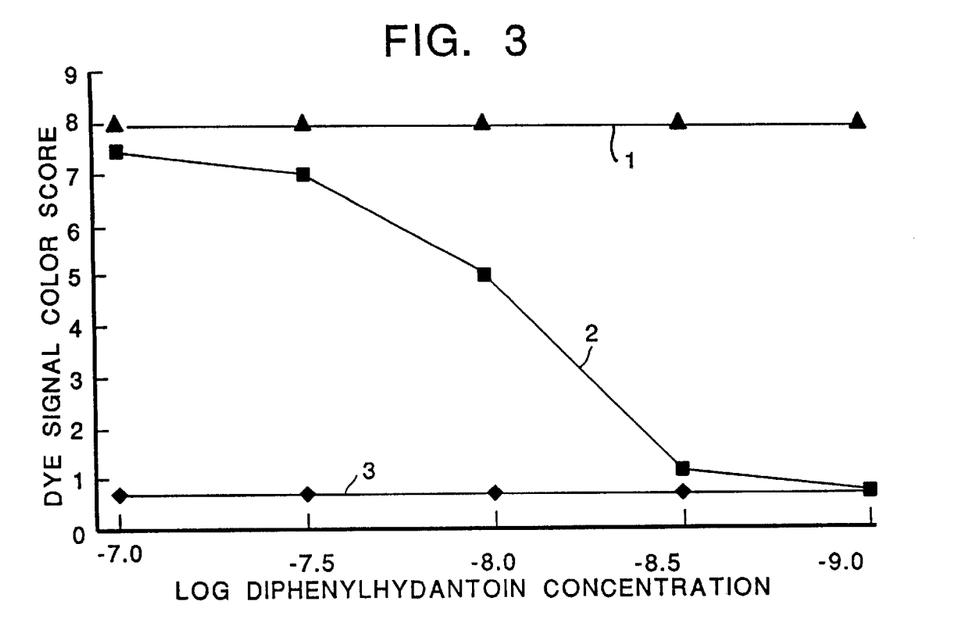
FIG. 3 is a graphical plot of dye signal color score versus log diphenylhydantoin concentration and is described in more detail in Example 2 below.
Figure 4:
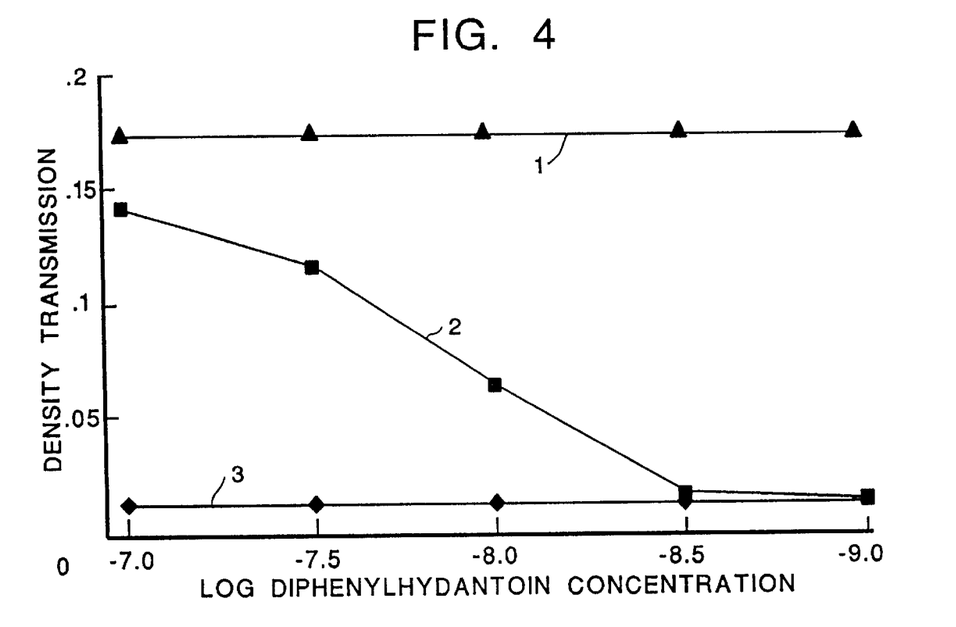
FIG. 4 is a graphical plot of dye signal density transmission versus log diphenylhydantoin concentration and is described in more detail in Example 2 below.

A titration of dye signal above background was observed as a function of diphenylhydantoin concentration with a detection limit of between $1 \times 10^{-9}$ and $3 \times 10^{-9}$ molar diphenylhydantoin. FIGS. 3 and 4 show the results of these assays in the form of dose response curves, including the positive and negative controls (curves 1 and 3, respectively), and the assay of the invention (curve 2). In FIG. 3, dye signal (observed color score from a color density chart) is plotted on the y-axis and diphenylhydantoin concentration [log (diphenylhydantoin)] is plotted on the x-axis. FIG. 4 is a similar plot with dye signal (density transmission) plotted on the y-axis.

EXAMPLE 3

Assay for Phenobarbital

The ligand phenobarbital was determined according to the method of the present invention as follows.

To an extraction device was added, in order:

N-[tris(hydroxymethyl)methyl]-2-aminoethanesulfonic acid buffer (0.103 ml, 0.1 molar, pH 7), anti-phenobarbital antibody reagent (0.167 ml, 0.6% solids, final concentration), and unlabelled phenobarbital solution (0.03 ml, various ligand concentrations), followed by incubation for 5 minutes at room temperature. Water-soluble phenobarbital-anti-inhibitor antibody conjugate (0.03 ml) was then added, followed by incubation for 5 minutes at room temperature. The filter cap was then placed on the tube.

Supernatant from the extraction tube was squeezed through the filter cap and applied to the test wells of the disposable test device containing the immobilized horseradish peroxidase reagent. Where target phenobarbital was present, the supernatant contained unbound water-soluble conjugate of phenobarbital and anti-inhibitor antibody.

After incubation for 5 minutes at room temperature, inhibitor antibody (100 μl) was added to the test wells, followed by another incubation for 5 minutes at room temperature. Three drops of the enzyme substrate solution were added. After incubation for 2 minutes at room temperature, the dye signal stop solution (3 drops) was added, and the resulting dye signal was evaluated.

Positive and negative control assays were similarly carried out as described in Example 1.

Figure 5:
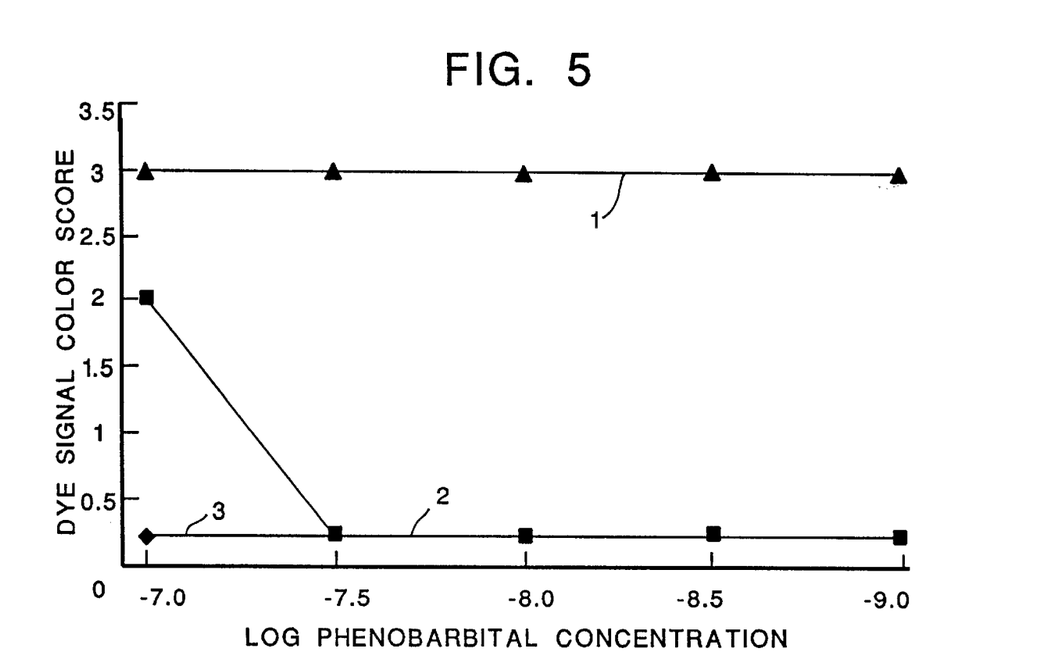
FIG. 5 is a graphical plot of dye signal color score versus log phenobarbital concentration and is described in more detail in Example 3 below.
Figure 6:
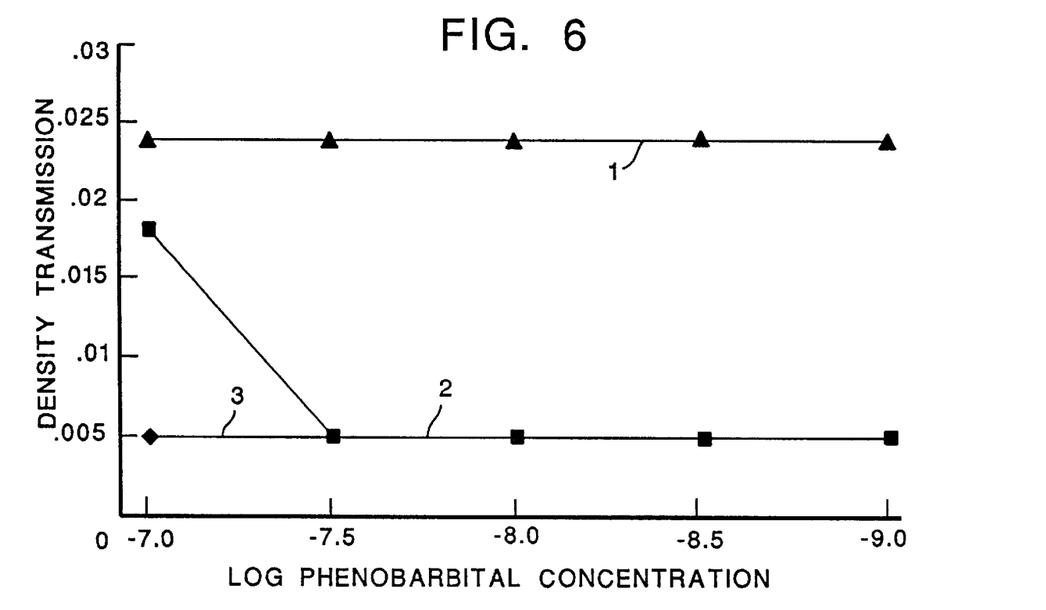
FIG. 6 is a graphical plot of dye signal density transmission versus phenobarbital concentration and is described in more detail in Example 3 below.

A titration of dye signal above background was observed as a function of phenobarbital concentration with a detection limit of between $1\times10^{-5}$ and $1\times10^{-6}$ molar phenobarbital. FIGS. 5 and 6 show the results of these assays in the form of dose response curves, including the positive and negative controls (curves 1 and 3, respectively), and the assay of the invention (curve 2). In FIG. 5, dye signal (observed color score from a color density chart) is plotted on the y-axis and phenobarbital concentration [log (phenobarbital)] is plotted on the x-axis. FIG. 6 is a similar plot with dye signal (density transmission) plotted on the y-axis.

EXAMPLE 4

Assay for Digoxin

The ligand digoxin was determined according to the method of the present invention as follows.

To an extraction device was added, in order:

N-[tris(hydroxymethyl)methyl]-2-aminoethanesulfonic acid buffer (0.090 ml, 0.1 molar, pH 7), anti-digoxin antibody reagent (0.180 ml, 0.6% solids, final concentration), and unlabelled digoxin solution (0.3 ml, various ligand concentrations), followed by incubation for 5 minutes at room temperature. Water-soluble digoxin-anti-inhibitor antibody conjugate (0.03 ml) was then added, followed by incubation for 5 minutes at room temperature. The filter cap was then placed on the tube.

Supernatant from the extraction tube was squeezed through the filter cap and applied to the test wells of the disposable test device containing the immobilized horseradish peroxidase reagent. Where target digoxin was present, the supernatant contained unbound water-soluble conjugate of digoxin and anti-inhibitor antibody.

After incubation for 5 minutes at room temperature, inhibitor antibody (100 μl) was added to the test wells, followed by another incubation for 5 minutes at room temperature. Three drops of the enzyme substrate solution were added. After incubation for 2 minutes at room temperature, the dye signal stop solution (3 drops) was added, and the resulting dye signal was evaluated.

Positive and negative control assays were similarly carried out as described in Example 1.

Figure 7:
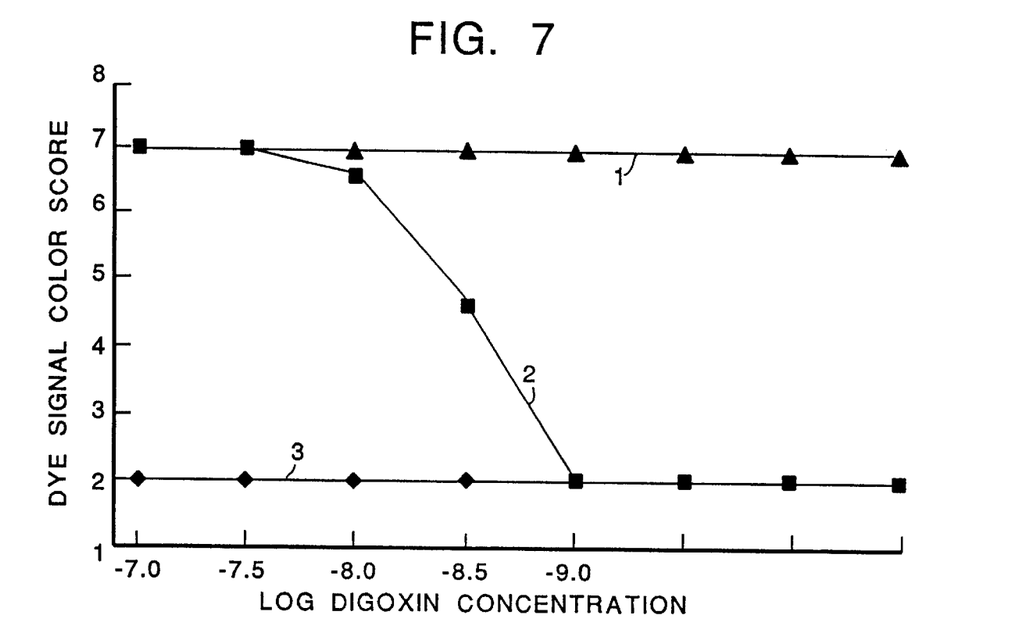
FIG. 7 is a graphical plot of dye signal color score versus log digoxin concentration and is described in more detail in Example 4 below.
Figure 8:
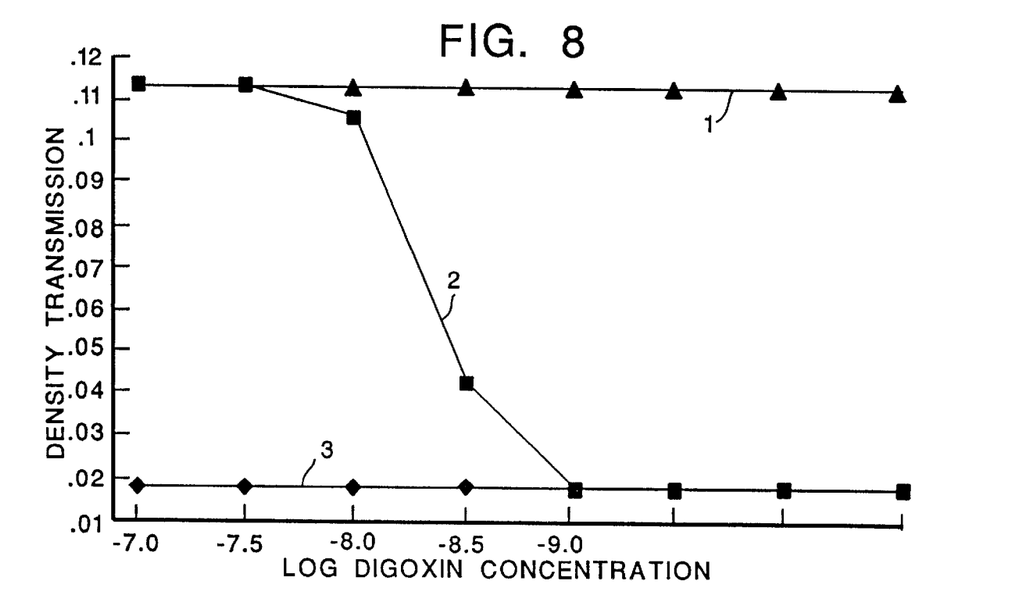
FIG. 8 is a graphical plot of dye signal density transmission versus log digoxin concentration and is described in more detail in Example 4 below.

A titration of dye signal above background was observed as a function of digoxin concentration with a detection limit of between $1\times10^{-7}$ and $3\times10^{-8}$ molar digoxin. FIGS. 7 and 8 show the results of these assays in the form of dose response curves, including the positive and negative controls (curves 1 and 3, respectively), and the assay of the invention (curve 2). In FIG. 7, dye signal (observed color score from a color density chart) is plotted on the y-axis and digoxin concentration [log(digoxin)] is plotted on the x-axis. FIG. 8 is a similar plot with dye signal (density transmission) plotted on the y-axis.

The invention has been described in detail with particular reference to preferred embodiments thereof, but it will be understood that variations and modifications can be effected within the spirit and scope of the invention.

We claim:

1. A specific binding method for the detection of a target specific binding ligand comprising the steps of:
   A) bringing together, in any order:
      1) a fluid sample suspected of containing a target specific binding ligand,
      2) an immobilized receptor for said target specific binding ligand, and
      3) a water-soluble conjugate of said target specific binding ligand and a first monoclonal antibody, said first monoclonal antibody having the following characteristics:
         a) specific to a reporter enzyme,
         b) a dissociation constant less than or equal to 100 nmolar, and
         c) binds to said reporter enzyme in such a manner that the enzymatic activity of said reporter enzyme is diminished by no more than about 20%, and wherein binding of said first monoclonal antibody substantially blocks binding of a second monoclonal antibody that specifically inhibits said reporter enzyme, to form a water-insoluble complex between said immobilized receptor and either said target specific binding ligand or said water-soluble conjugate,
   B) separating said water-insoluble complex formed in step A) from a supernatant containing any uncomplexed water-soluble conjugate,
   C) bringing together, in any order:
      (i) a sample of said supernatant containing any uncomplexed water-soluble conjugate,
      (ii) an immobilized form of said reporter enzyme, and
      (iii) a second monoclonal antibody having the following characteristics:
         a) specific to said reporter enzyme,
         b) a dissociation constant less than or equal to 125 nmolar, and
         c) binds to said reporter enzyme in such a manner as to inhibit the enzymatic activity of said reporter enzyme by at least about 80%, to form a water-insoluble complex between said immobilized reporter enzyme and said uncomplexed water-soluble conjugate or said second antibody, or both and
   D) contacting said immobilized reporter enzyme with a solution comprising substrate for said enzyme, and
   E) detecting the signal generated from said immobilized reporter enzyme as a determination of said target specific binding ligand in said fluid sample.

2. The method of claim 1 wherein said reporter enzyme and said receptor are immobilized on separate polymeric particles.

3. The method of claim 1 wherein said reporter enzyme is a peroxidase, alkaline phosphatase, creatine kinase, glucose oxidase, urease, β-galactosidase or glucose-6-phosphate dehydrogenase.

4. The method of claim 3 wherein said reporter enzyme is horseradish peroxidase.

5. The method of claim 1 wherein:

said second monoclonal antibody has a dissociation constant of less than or equal to 10 nmolar, and binds to said reporter enzyme in such a manner as to inhibit at least about 95% of the enzymatic activity of said reporter enzyme, and said first monoclonal antibody has a dissociation constant less than or equal to about 5 nmolar, and binds to said reporter enzyme in such a manner that the enzymatic activity of said reporter enzyme is diminished by no more than about 6%.

6. The method of claim 1 wherein said detection step E) is carried out by evaluating a colorimetric signal generated from said reporter enzyme in the presence of a suitable substrate.

7. The method of claim 1 for the detection of a low molecular weight target specific binding ligand wherein said receptor is an antibody specific to said low molecular weight target specific binding ligand.

8. The method of claim 1 for the detection of prostaglandin $E_2$ ($PGE_2$) wherein said receptor is an antibody specific to $PGE_2$.

9. The method of claim 1 wherein:

said fluid sample and said immobilized receptor are brought together prior to contact with said water-soluble conjugate, said water-insoluble complex formed in step A) is separated from said uncomplexed water-soluble conjugate in said supernatant by filtration, and said supernatant sample and said immobilized reporter enzyme are brought together prior to contact with said second monoclonal antibody.

* * * * *